(12) United States Patent
Johnson (10) Patent No.: US 9,044,481 B2
(45) Date of Patent: Jun. 2, 2015

(54) LIPIDATED OXOADENINE DERIVATIVES

(75) Inventor: David Johnson, Hamilton, MT (US)

(73) Assignee: GlaxoSmithKline Biologicals S.A., Rixensart (BE)

( * ) Notice: Subject to any disclaimer, the term of this patent is extended or adjusted under 35 U.S.C. 154(b) by 415 days.

(21) Appl. No.: 13/389,307

(22) PCT Filed: Aug. 6, 2010

(86) PCT No.: PCT/US2010/044703
§ 371 (c)(1),
(2), (4) Date: Feb. 7, 2012

(87) PCT Pub. No.: WO2011/017611
PCT Pub. Date: Feb. 10, 2011

(65) Prior Publication Data
US 2012/0135963 A1    May 31, 2012

Related U.S. Application Data (60) Provisional application No. 61/232,132, filed on Aug. 7, 2009.

(51) Int. Cl.
*C07D 403/06* (2006.01)
*A61K 31/52* (2006.01)
*A61K 31/522* (2006.01)
*A61K 47/48* (2006.01)

(52) U.S. Cl.
CPC .............. *A61K 31/52* (2013.01); *C07D 403/06* (2013.01); *A61K 31/522* (2013.01); *A61K 47/48053* (2013.01); *A61K 47/48123* (2013.01); *A61K 47/48815* (2013.01)

(58) Field of Classification Search
None
See application file for complete search history.

(56) References Cited

U.S. PATENT DOCUMENTS

| 6,028,076 A | 2/2000 | Hirota et al. |
|---|---|---|
| 2006/0189550 A1 | 8/2006 | Jiang et al. |
| 2008/0008682 A1 | 1/2008 | Chong et al. |
| 2009/0192153 A1 | 7/2009 | Hashimoto et al. |
| 2011/0135670 A1* | 6/2011 | Campos et al. ............ 424/184.1 |
| 2011/0135671 A1* | 6/2011 | Bazin-Lee et al. ......... 424/184.1 |

FOREIGN PATENT DOCUMENTS

WO   2008/114008   9/2008

OTHER PUBLICATIONS

Bell et al., Proceedings of the National Academy of Science, The molecular structure of the Toll-like receptor 3 ligand-binding domain, Proceedings of the National Academy of Science, vol. 102, pp. 10976-10980, (2005).
Chan, Michael et al; Synthesis and Immunological Characterization of Toll-Like Receptor 7 Agonists Conjugates; Bioconjugates Chem, 2009, Vo. 20, pp. 1194-1200.
European Office Action dated Oct. 16, 2013.

* cited by examiner

*Primary Examiner* — Michael Barker
(74) *Attorney, Agent, or Firm* — Michael M. Conger (57) ABSTRACT

Provided are novel lipidated oxoadenines which are useful as immunostimulators and adjuvants and are shown to be inducers of interferon-a and other immunostimulatory cytokines.

12 Claims, 4 Drawing Sheets

LIPIDATED OXOADENINE DERIVATIVES

This application is filed pursuant to 35 U.S.C. §371 as a United States National Phase Application of International Patent Application Serial No. PCT/US2010/0447038 filed Jun. 8, 2010, which claims priority to U.S. Provisional Application No. 61/232,132 filed 7 Aug. 2009 the contents of which are incorporated herein by reference.

BACKGROUND OF THE INVENTION

The present invention relates to novel adjuvant compounds, processes for their preparation, compositions containing them, and their use as vaccine adjuvants.

The refinement and simplification of microbial vaccines and the use of synthetic and recombinant subunit antigens to improve vaccine manufacturability and safety has resulted in a decrease in vaccine potency. This has led to studies on the co-administration of adjuvants with antigens to potentiate vaccine activity and the weak immunogenicity of synthetic and recombinant epitopes. Adjuvants are additives that enhance humoral and/or cell-mediated immune responses to a vaccine antigen. The design of vaccine adjuvants, however, has historically been difficult because of the complex nature of the molecular mechanisms involved in immune system function. Although the addition of microbial components has long been known to enhance adaptive immune responses, only recently was it shown that toll-like receptors (TLRs) on cells involved in immune surveillance, such as epithelial and dendritic cells, engage many of these microbial products via so-called "pathogen-associated patterns" or PAMPs. Many vaccine adjuvants and stand-alone immunomodulators appear to interact with members of the TLR family.

Of the 10 known TLRs that have been identified in humans, five are associated with the recognition of bacterial components (TLRs 1, 2, 4, 5, 6) and four others (TLRs 3, 7, 8, 9) appear to be restricted to cytoplasmic compartments and are involved in the detection of viral RNA (TLRs 3, 7, 8) and unmethylated DNA (TLR9) (Iwasaki, A., *Nat Immunol* 2004, 5, 987) Activation of TLRs regulates intracellular signaling pathways and leads to gene expression via interaction with intracellular adapter molecules such as MyD88, TRIF, TIRAP, and TRAM (Akira, S. *Nat Rev Immunol* 2004, 4, 499; Takeda, K. *Semin Immunol* 2004, 16, 3). These adapter molecules can differentially regulate the expression of inflammatory cytokines/chemokines and type I interferons (IFNα/β), which can lead to the preferential enhancement of antigen-specific humoral and cell-mediated immune responses (Zughaier, S. *Infect Immun* 2005, 73, 2940). Humoral immunity is the major line of defense against bacterial pathogens, whereas the induction of cytotoxic T lymphocytes (CTLs) appears to be crucial for protective immunity in the case of viral disease and cancer.

In the case of TLR7 and TLR8 activation, a few different classes of small molecule mimetics of the natural (U- and/or G-rich) viral ssRNA ligands have been identified. These include certain antiviral compounds related to oxidized guanosine metabolites (oxoguanosines), which primarily interact with TLR7 (Heil, F. *Eur J Immunol* 2003, 33, 2987; Hemmi, 2002) and derivatives of adenine which engage TLR7 and/or TLR8. The immune stimulating ability of these compounds has been attributed to the TLR/MyD88-dependent signaling pathways and the production of cytokines, including IL-6 and type I (particularly interferon-α) and II interferons. TLR7 or TLR8 activation leads to the upregulation of co-stimulatory molecules (e.g. CD-40, CD-80, CD-86) and class I and II MHC molecules on dendritic cells (DCs). DCs are the principal cells of the immune system involved in uptake and presentation of antigens to T lymphocytes. Plasmacytoid dendritic cells (pDCs), which preferentially express TLR7, are professional interferon-α producing cells; whereas mDCs express TLR8 only. TLR8 activation on mDCs leads to the preferential production of pro-inflammatory cytokines such as IL-12, TNF-α, and IFN-γ and cell-mediated immunity (CMI). It has been shown that TLR7 agonists are more effective at generating IFN-α and INF-regulated cytokines, whereas TLR8 agonists, which lead to the reversal of CD4+ regulatory (Treg) cell function, are more effective at inducing proinflammatory cytokines such as TNF-α and IL-12, suggesting that TLR7 activation may be more important for antibody responses (Th2-type responses) while TLR8 activation should induce CMI or Th1-type immune responses (Gordon *J Immunol* 2005, 1259).

One class of TLR-active adenine derivatives that has received a considerable amount of attention are the oxoadenines. The oxoadenines typically contain a hydroxyl group in the 8-position of the adenine ring (often shown in 8-keto/oxo tautomeric form), various substituents at the 2- and 9-positions, and an unsubstituted aromatic amino group in the 4-position. As with other IFN-inducing adenine derivatives such as the imidazoquinolines, an unsubstituted aromatic amino group is thought to be essential for IFN-inducing activity. Many of the oxoadenines, which were initially developed to overcome certain side effects associated with the imidazoquinolines, have been shown to be considerably more potent than prototypical imidazoquinolines such as imiquimod and resiquimod with respect to IFN-inducing activity in vitro and in vivo but devoid of emetic activity, a major clinical side effect with imidazoquinolines. For example, the oxoadenine SM360320 is currently under preclinical development against HCV and has been shown to suppress the replication of HCV in human hepatocytes by type I IFN induction as well as through an IFN-independent mechanism (Lee *PNAS* 2006, 103, 1828). Nevertheless, despite the fact that the oxoadenine class appears to exhibit better overall toxicity/bioactivity profiles than imidazoquinolines, administration of SM360320 to mice by various routes leads to systemic sickness response, mediated in part by inflammatory cytokines released by mast cells (Hayashi *Am J Physiol Regul Integr Comp Physiol* 2008, 295, R123). In fact, the large immunological "footprint" of TLR7 agonists in general has led to concerns over toxicity and to suspension of clinical trials in many cases (Strominger *Brain Res Bull* 2001, 55, 445; Schmidt *Nat Biotech* 2007, 25, 825).

Since most of the TLR7/8 agonists currently under development often display toxic properties, are unstable, and/or have insubstantial immunostimulatory effects, the discovery and development of effective and safe vaccine adjuvants that activate TLR7 and/or TLR8 is essential for improving the safety and efficacy of existing and new vaccines.

BRIEF DESCRIPTION OF THE INVENTION

Herein we describe novel lipidated oxoadenines comprising a nitrogen heterocyclyl-substituted oxoadenine molecule covalently linked to a phospho- or phosphonolipid in such a manner so as to facilitate uptake into immune cells and enhance endosomal TLR7/8 activation and antigen presentation when administered alone or in depot formulation with an antigen. Enhanced immune responses with compounds of the subject invention are possibly due to direct interaction of compounds of formula (I) with endosomal TLR7 and/or TLR8 or other molecular receptors and/or interaction of an active metabolite after enzymatic action with TLR7 and/or TLR8 or other molecular receptors.

The compounds of the invention have been shown to be inducers of interferon-α and other immunostimulatory cytokines and may possess an improved activity-toxicity profile in comparison to known cytokine inducers when used as adjuvants for vaccine antigens in the therapeutic or prophylactic treatment of infectious diseases and cancer. These compounds are also novel per se.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

"Alkyl" refers to monovalent saturated aliphatic hydrocarbyl groups having from 1 to 14 carbon atoms and, in some embodiments, from 1 to 6 carbon atoms. "$(C_x\text{-}C_y)$alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O) and alkenyl-C(O).

"Amino" refers to the group —NHR[4] where R[4] is independently selected from hydrogen, alkyl, alkenyl, alkynyl, aryl, cycloalkyl, heteroaryl and heterocyclic.

"Cycloalkyl" refers to a saturated or partially saturated cyclic group of from 3 to 14 carbon atoms and no ring heteroatoms.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. It is understood that the above definitions are not intended to include impermissible substitution patterns (e.g., methyl substituted with 5 fluoro groups). Such impermissible substitution patterns are well known to the skilled artisan.

The compounds of the subject invention are adjuvant molecules that comprise a nitrogen heterocyclyl-substituted oxoadenine molecule covalently linked to a phospho- or phosphonolipid group. The compounds of the subject invention are described generally by Formula (I):

(I)

wherein $R_1$=$C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino, $C_{1-6}$alkoxy$C_{1-6}$alkoxy; and optionally terminally substituted with a hydroxyl, amino, thio, hydrazino, hydrazido, azido, acetylenyl, carboxyl, or maleimido group;

n=0-6;

Het is a four-, five-, or six-membered saturated nitrogen heterocycle wherein

X, Y=CH or N, and at least one of X and Y is a nitrogen atom;

Q=O, NH, or covalent bond;

Z=O, $CH_2$, $CF_2$ or covalent bond;

W=O, S;

m=0-6;

p=1 or 2;

q=0 or 1;

A= wherein $R_2$=H or saturated or unsaturated $C_4$-$C_{24}$ alkyl or acyl;

$R_3$=saturated or unsaturated $C_4$-$C_{24}$ alkyl or acyl;

or a pharmaceutically acceptable salt thereof.

In one preferred embodiment, the compounds of the subject invention are described generally by Formula II:

(II)

wherein $R_1$ = $C_{1-6}$alkylamino, $C_{1-6}$alkoxy, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino, $C_{1-6}$alkoxy$C_{1-6}$alkoxy; branched or unbranched;

n=0-6;

X=CH or N;

Q=O, NH, or covalent bond;

Z=O, $CH_2$, $CF_2$ or covalent bond;

W=O, S;

m=0-6;

p=1 or 2;

q=0 or 1;

$R_2$=H or saturated or unsaturated $C_4$-$C_{24}$ alkyl or acyl;

$R_3$=saturated or unsaturated $C_4$-$C_{24}$ alkyl or acyl;

or pharmaceutically acceptable salts thereof.

The compounds of the subject invention are prepared from known oxoadenine intermediates III as shown in one embodiment in Scheme 1 by (1) alkylation of III with a suitably protected nitrogen heterocyclyl alkyl bromide IV, (2) simultaneous deprotection of the N- and O-protecting groups of V under acidic conditions, and (3) either direct phosphatidylation of the N-heterocyclic substituent of VI (m=0, Q=single bond) with VII to give compounds of the subject invention VIII wherein m=0 and Q=single bond; or, alternatively, N-alkylation of VI with an N- or O-protected amino- or hydroxy-alkyl bromide followed by deprotection and O- or N-phosphatidylation with VII to give compounds of the subject invention VIII wherein m=2-6 and Q=O or NH.

Scheme 1

III

In one further aspect, the invention comprises a compound according to the structure of Formula IX, (IX)

wherein $R_1$ is selected from the group consisting of $C_{1-6}$alkyl, $C_{1-6}$alkylamino, $C_{1-6}$alkoxy, $C_{1-6}$alkoxy$C_{1-6}$alkylamino, $C_{1-6}$alkoxy$C_{1-6}$alkoxy;

n is 0-2;

X is CH or N

Q is O, NH, or covalent bond;

m is 0-2;
q is 0;
$R_2$ is H or saturated or unsaturated $C_4$-$C_{24}$ alkyl or acyl, and
$R_3$ is saturated or unsaturated $C_4$-$C_{24}$ alkyl or acyl;
or pharmaceutically acceptable salts thereof.

In another aspect, the invention comprises a compound according to the structure of Formula IX, wherein
$R_1$ is $C_{1-6}$alkoxy,
n is 0-2
X is CH or N;
Q is O, NH
m is 0-2
q is 0
$R_2$ is H or saturated or unsaturated $C_4$-$C_{24}$ alkyl or acyl, and
$R_3$ is saturated or unsaturated $C_4$-$C_{24}$ alkyl or acyl;
or pharmaceutically acceptable salts thereof.

EXAMPLE 1

Compound A1

Preparation of 6-Amino-2-butoxy-9-[N-(2-(1,2-dipalmitoyl-sn-glycero-3-phospho)ethyl)-4-piperidinylmethyl]-8-hydroxypurine (Compound (II), $R_1$=n-butoxy, n=1, X=CH, Q=O, Z=O, W=O, m=2, p=1, $R_1$=$R_2$=n-$C_{15}H_{31}$CO)

(1) Potassium carbonate (0.65 g) was added to a solution of 6-amino-2-butoxy-8-methoxypurine (0.55 g) in dry N,N-dimethylformamide (DMF, 5.5 mL) and the resulting reaction mixture was heated at 60° C. for 1 h. 1,1-Dimethylethyl 4-(bromomethyl)-1-piperidinecarboxylate (0.5 g) was added using additional DMF (1.5 mL) to transfer the residual bromide and the reaction mixture was stirred at 50° C. for 3 h. After 16 h at room temperature, heating was continued at 50° C. for another 5 h to complete the reaction. Water was then added and the resulting mixture was extracted with three times with ethyl acetate (EtOAc). The combined organic extracts were washed with water, dried ($Na_2SO_4$), and concentrated. Flash chromatography on silica gel with MeOH—$CHCl_3$ (gradient elution; 1:99→2.5:97.5) afforded 0.64 g (94%) of 1,1-dimethylethyl 4-[6-amino-2-butoxy-8-methoxy-purin-9-yl]methyl-1-piperidinecarboxylate as a yellow solid. $^1$H NMR ($CDCl_3$): δ 5.14 (s, 2H), 4.27 (t, 2H), 4.11 (s, 3H), 3.81 (d, 2H), 2.65 (m, 2H), 2.03 (m, 1H), 1.77 (p, 3H), 1.57-1.45 (m, 14H), 1.26-1.17 (m, 2H), 0.97 (t, 3H).

(2) To a solution of the compound prepared in (1) above (0.63 g) in MeOH (16 mL) was added a 4.0 M HCl in dioxane (5.3 mL). After stirring 4.5 h at room temperature, the reaction mixture was concentrated and dried under high vacuum. Flash chromatography on silica gel with $CHCl_3$-MeOH—$H_2O$ (gradient elution; 90:10:1→75:25:1) afforded 0.404 g (85%) of 6-amino-2-butoxy-9-(4-piperidinylmethyl)-8-hydroxypurine hydrochloride as a white solid. $^1$H NMR ($CDCl_3$): δ 4.84 (s, 5H), 4.27 (t, 2H), 3.79 (d, 2H), 3.40 (d, 2H), 2.96 (t, 2H), 2.21 (m, 1H), 1.92 (d, 2H), 1.75 (m, 2H), 1.60-1.47 (m, 4H), 1.00 (t, 3H (3) To a solution of the compound prepared in (2) above (1.24 g) in DMF (12.6 mL; 0.25 M) was added $K_2CO_3$ (1.74 g). The resulting mixture was heated to 60° C. for 1 h, treated with 2-bromoethoxy-tert-butyldimethylsilane (0.81 mL), and then heated at 50° C. for 18 h. The cooled reaction mixture was quenched with water, transferred to a separatory funnel, and extracted three times with EtOAc. The combined organic layers were dried ($Na_2SO_4$) and concentrated. Flash chromatography on silica gel afforded 1.25 g (83%) of 6-amino-2-butoxy-9-[N-(2-O-tert-butyldimethylsilyl)ethyl)-4-piperidinyl-methyl-]-8-hydroxypurine as an off-white solid. NMR ($CDCl_3$—$CD_3OD$, 400 MHz): δ 4.26 (m, 4H), 3.75 (m, 4H), 3.36 (m, 2H), 2.96 (m, 2H), 2.54 (t, 2H), 1.92 (bs, 1H), 1.73 (m, 2H), 1.66 (m, 2H), 1.40-1.51 (m, 5H), 0.98 (t, 3H), 0.89 (m, 9H), 0.06 (s, 6H).

(4) To a solution of the compound prepared in (3) above (2.74 g) in MeOH (41 mL) was added a 4.0 M HCl in dioxane (5.7 mL). After stirring 0.5 h at room temperature, the reaction mixture was concentrated and dried under high vacuum. Flash chromatography on silica gel with $CHCl_3$-MeOH—$H_2O$ (gradient elution; 90:10:1→75:25:1) afforded 2.29 g (100%) of 6-amino-2-butoxy-9-(N-(2-hydroxyethyl)-4-piperidinylmethyl)-8-hydroxypurine hydrochloride as a white solid. $^1$H NMR ($CD_3OD$, 400 MHz): δ 4.53 (t, 2H), 3.87 (m, 4H), 3.66 (d, 2H), 3.22 (m, 2H), 3.01 (t, 2H), 2.21 (m, 1H), 1.98 (d, 2H), 1.81 (m, 2H), 1.68 (m, 2H), 1.52 (m, 2H), 1.01 (t, 3H).

(5) A solution of the compound prepared in (4) above (51 mg) and 1,2-dipalmitoyl-sn-glyceryl hydrogenphosphonate (93 mg; compound V1, $R_1$=$R_2$=palmitoyl) in pyridine (6.4 mL) was treated pivaloyl chloride (0.047 mL) and the resulting reaction mixture was stirred at room temperature for 6 h. A solution of iodine (129 mg) in pyridine-water (19:1, v/v) was then added and the reaction mixture was stirred at room temperature for 1 h, diluted with $CHCl_3$, and then quenched with 1 M $Na_2S_2O_5$. The aqueous layer was extracted twice with $CHCl_3$ and the combined organic layers were washed with 1 M triethylammonium borate (pH 8). The organic layer was dried ($Na_2SO_4$) and concentrated. Flash chromatography on silica gel with $CHCl_3$-MeOH-$Et_3N$ (gradient elution; 90:10:1→75:25:1) afforded 38 mg (30%) of 6-amino-2-butoxy-9-[N-(2-(1,2-dipalmitoyl-sn-glycero-3-phospho)ethyl-4-piperidinylmethyl]-8-hydroxypurine as an off-white solid. $^1$H NMR ($CDCl_3$—

CD$_3$OD, 400 MHz): δ 5.17 (bs, 1H), 4.32 (dd, 1H), 4.20-4.09 (m, 5H), 3.98 (br t, 2H), 3.69 (br d, 3H), 3.23 (br s, 1H), 1.86 (br s, 4H), 1.69 (m, 2H), 1.53 (br s, 4H), 1.42 (dd, 2H), 1.20 (m, 48H), 0.91 (t, 3H), 0.83 (t, 6H); HRMS calcd for [M–H]$^-$ C$_{52}$H$_{94}$N$_6$O$_{10}$P 993.6768. found 993.6782.

EXAMPLE 2

Compound A2

Preparation of 6-Amino-2-butoxy-9-[N-(2-(1,2-dipalmitoyl-sn-glycero-3-phosphoramido)ethyl)-4-piperidinylmethyl]-8-hydroxypurine (Compound (II), R$_1$=n-butoxy, n=1, X=CH, Q=NH, Z=O, W=O, m=2, p=1, R$_1$=R$_2$=n-C$_{15}$H$_{31}$CO)

(1) In the same manner as described in Example 1-(3), the compound prepared in Example 1-(2) (107 mg) was alklyated in DMF (1.1 mL) with 2-(tert-butoxycarbonylamino)ethyl bromide (67 mg) in the presence of K$_2$CO$_3$ to give 84 mg (67%) of 1,1-dimethylethyl 4-[6-amino-2-butoxy-8-methoxy-purin-9-yl]methyl-1-piperidinyl-ethylaminylcarboxylate as an off-white solid. $^1$H NMR (CDCl$_3$—CD$_3$OD, 400 MHz): δ 4.25 (t, 2H), 3.73 (d, 2H), 3.38 (m, 2H), 3.20 (m, 2H), 2.89 (m, 2H), 2.44 (m, 2H), 1.97 (t, 3H), 1.75 (m, 2H), 1.66 (m, 2H), 1.42-1.51 (m, 11H), 0.97 (t, 3H).

(2) In the same manner as described in Example 1-(4), the compound prepared in (1) above (83 mg) was N-deprotected with 4 N HCl in dioxane to give 58 mg (74%) of 6-amino-2-butoxy-9-[N-(2-aminoethyl)4-piperidinylmethyl]-8-hydroxypurine dihydrochloride as a an off-white solid. $^1$H NMR (DMSO-d$_6$, 400 MHz): δ 4.15 (t, 2H), 3.58 (d, 2H), 2.88 (t, 2H), 2.81 (d, 2H), 2.46 (t, 2H), 1.91 (t, 2H), 1.79 (m, 1H), 1.64 (m, 2H), 1.52 (m, 2H), 1.39 (dd, 2H), 1.28 (m, 2H), 0.91 (t, 3H).

(3) A solution of 1,2-dipalmitoyl-sn-glyceryl hydrogenphosphonate (167 mg; compound V1, R$_1$=R$_2$=palmitoyl) in pyridine (11.3 mL) was treated with chlorotrimethylsilane (0.087 mL) and triethylamine (0.126 mL) and the resulting reaction mixture was stirred at room temperature for 0.5 h. A suspension of the compound prepared in (2) above (37 mg) and triethylamine (0.126 mL) in pyridine (2.3 mL) was added to the reaction mixture followed by the addition of. iodine (75 mg) The reaction mixture was stirred at room temperature for 2 h, concentrated, and co-evaporated twice with toluene. Flash chromatography on silica gel with CHCl$_3$-MeOH-Et$_3$N (gradient elution; 90:10:1→75:25:1) afforded 39 mg (18%) of 6-amino-2-butoxy-9-[N-(2-(1,2-dipalmitoyl-sn-glycero-3-phosphoramido)ethyl-4-piperidinylmethyl]-8-hydroxypurine as an orange glassy solid. Rf (CHCl$_3$—CH$_3$OH—H$_2$O—NH$_4$OH)=0.68.

EXAMPLE 3

Compound A3

Preparation of 6-Amino-2-butoxy-9-[1-(1,2-dipalmitoyl-sn-glycero-3-phosphoramido)-4-piperazinylethyl]-8-hydroxypurine (Compound (II), R$_1$=n-butoxy, n=2, X=N, Q=single bond, Z=O, W=O, m=0, p=1, R$_1$=R$_2$=n-C$_{15}$H$_{31}$CO)

(1) In the same manner as described in Example 1-(1), 6-amino-2-butoxy-8-methoxypurine (131 mg) was alkylated in DMF with 1,1-dimethylethyl 4-(bromoethyl)-1-piperazinecarboxylate (120 mg) in the presence of $K_2CO_3$ to give 124 mg (74%) of 1,1-dimethylethyl 4-[6-amino-2-butoxy-8-methoxy-purin-9-yl]ethyl-1-piperazinecarboxylate as a light yellow solid. $^1$H NMR ($CDCl_3$—$CD_3OD$, 400 MHz): δ 5.66 (d, 2H), 4.25 (t, 2H), 4.05 (t, 2H), 4.10 (s, 3H), 3.35 (bs, 4H), 2.71 (t, 2H), 2.46 (bs, 4H), 1.76 (m, 2H), 1.48 (m, 2H), 1.45 (s, 9H), 0.96 (t, 3H).

(2) In the same manner as described in Example 1-(2), the compound prepared in (1) above (124 mg) was N-deprotected with 4.0 M HCl in dioxane to give 87 mg (77%) of 6-amino-2-butoxy-9-(4-piperazinylethyl)-8-hydroxypurine hydrochloride as an off-white solid. $^1$H NMR ($CD_3OD$, 400 MHz) δ 4.26 (t, 2H), 3.96 (m, 2H), 3.11 (m, 5H), 2.78 (m, 7H), 1.73 (m, 2H), 1.48 (m, 2H), 1.38 (m, 1H), 0.98 (t, 3H); $^{13}$C NMR 161.8, 155.6, 150.8, 149.7, 100.1, 68.8, 55.9, 50.8, 44.2, 37.7, 31.9, 20.1, 14.1; HRMS calcd for $[M+H]^+$ $C_{15}H_{25}N_7O_2$ 336.2136, found 336.2148.

(3) In the same manner as described in Example 2-(3), the compound prepared in (2) above (288 mg) was phosphatidylated with 1,2-dipalmitoyl-sn-glyceryl hydrogenphosphonate (518 mg) to give 313 mg (46%) of 6-amino-2-butoxy-9-[1-(1,2-dipalmitoyl-sn-glycero-3-phosphoramido)-4-piperazinylethyl]-8-hydroxypurine as a tan solid. $^1$H NMR ($CDCl_3$—$CD_3OD$, 400 MHz): δ 5.11 (br s, 1H), 4.28 (d, 1H), 4.12-4.01 (m, 5H), 3.76 (br s, 2H), 3.60-2.60 (m, 11H), 2.21 (m, 4H), 1.65 (m, 2H), 1.49 (m, 4H), 1.39 (q, 2H), 1.17 (m, 48H), 0.88 (t, 3H), 0.81 (t, 6H); HRMS calcd for $[M-H]^-$ $C_{50}H_{92}N_7O_9P$ 964.6616, found 964.6600.

We evaluated the capacity of TLR7 ligands to promote various aspects of the immune response in mice. Innate immunity was specifically investigated to conclude whether lipidated TLR7 compounds were able to induce innate chemokines and pro-inflammatory cytokines. This innate immune response provides the body with initial, non-specific protection against pathogens. Among these innate chemokines and cytokines, type I IFN is thought to be required for the programming of naïve CD8 T-cell with respect to survival, differentiation and memory development. Mice studies have also suggested that the magnitude and duration of inflammation regulates the rate at which CD8+ T-cells acquire memory characteristics.

EXAMPLE 4

TLR7-DPPC Liposome Preparation 10.4 ml of lipidated-TLR7-L A1 at 10 mg/ml in chloroform were transferred into a round-bottomed glass vial. To this vial were added 18.4 ml of DPPC solubilised in chloroform at 100 mg/ml. 21.9 ml of lipidated-TLR7-L compound A3 solubilized at 5 mg/ml in chloroform were transferred into a round-bottomed glass vial. To this vial were added 20 ml of DPPC solubilised in chloroform at 100 mg/ml. Chloroform was evaporated in a Büchi Rotavapor under slow decrease of pressure. The obtained film was further dessicated at least overnight in a dessicator under vacuum. After that, the lipid film was slowly hydrated on an orbital shaker (maximal speed: 250 rpm) using 50 mM $PO_4$-100 mM NaCl, pH 7 buffer pre-heated at 60° C.

After completion of resuspension, a swelling step was carried out in order to further increase the phospholipid hydration, it consists of incubating the preparation at room temperature. The suspension was then pre-homogenized using a rotor-stator homogenizer (X620 CAT) for 12 min at 8000 rpm.

Microfluidization was then carried out using a microfluidizer (Model 110S-Serial 90181-Microfluidics Corporation) at 6 bars while keeping the microfluidization chamber at about 40° C. Sterile filtration was achieved on a PES filter (GD/X 0.2 μm, 25 mm, Whatman).

EXAMPLE 5

20080672: SIV-p27 Model—DPPC Liposomes—A3 and A1

Figure 1:
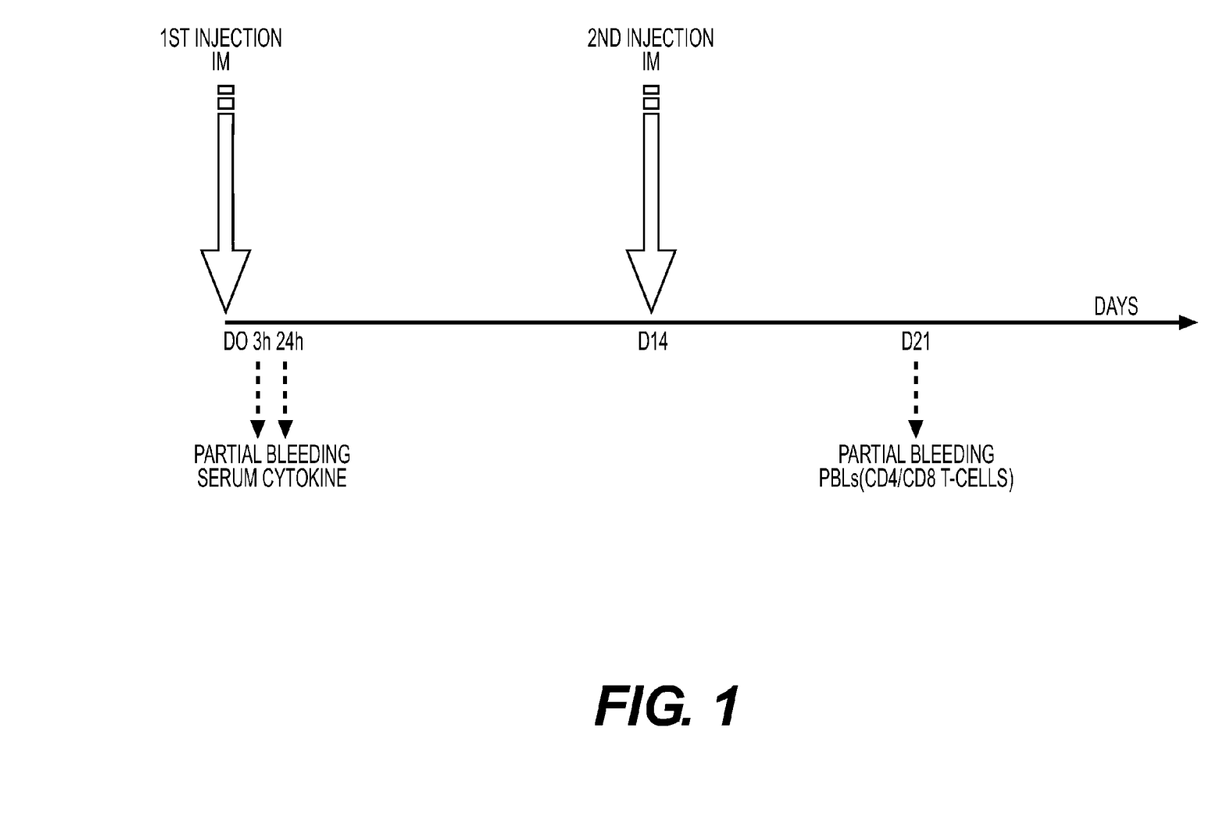
FIG. 1 shows a protocol for evaluating vaccines comprising lipidated oxoadenines in C57BU6 mice.

Lipidated molecules A3 and A1 were evaluated in vivo. The SIV-p27-containing formulations summarized in Table 1 were used to vaccinate 6-8 week old C57BL/6 female mice (10/group). The mice received two intramuscular injections of 50 μl, 14 days apart and were bled at different time points after prime and boost as illustrated in FIG. 1.

The innate and adaptive immune responses induced by the formulations containing the TLR7 agonists and the proprietary AS01B adjuvant (QS21+MPL) were also compared to the one induced by the corresponding AS01B-containing formulations and empty DPPC liposomes.

TABLE 1

SUMMARY TABLE OF THE FORMULATIONS CONTENT

| Vaccinated groups | SIV-p27 | MPL | QS21 | A3* | A1* | DPPC | CpG |
|---|---|---|---|---|---|---|---|
| p27 1B + empty DPPC | 5 | 5 | 5 | — | — | 3970 | — |
| p27 1B + 200 μg A3-DPPC | 5 | 5 | 5 | 200 | — | 3235 | — |
| p27 1B + 45 μg A3-DPPC | 5 | 5 | 5 | 45 | — | 726 | — |
| p27 1B + 4.5 μg A3-DPPC | 5 | 5 | 5 | 4.5 | — | 73 | — |
| p27 1B + 200 μg A1-DPPC | 5 | 5 | 5 | — | 200 | 2519 | — |
| p27 1B + 45 μg A1-DPPC | 5 | 5 | 5 | — | 45 | 566 | — |
| p27 1B + 4.5 μg A1-DPPC | 5 | 5 | 5 | — | 4.5 | 57 | — |
| p27 1B + CpG | 5 | 5 | 5 | — | — | — | 42 |
| naive | — | — | — | — | — | — | — |

All compounds are in μg unless otherwise stated.

*Doses are based on the amount of TLR7-L used to manufacture the A1-DPPC and A3-DPPC liposomes. The real injected doses might be lower due to loss during filtration

Different profiles of cytokines were observed between the AS01B reference group and the groups immunized with TLR7-L containing formulations. Shortly after injection (3 h), IFN-alpha was detected in a dose-dependent manner in the sera of mice immunized with both TLR7-L when they were formulated within a DPPC-liposome (FIG. 1). Such seric IFNa innate response was not observed when the TLR7-L were formulated in a DOPS/DOPC-liposome (data not shown).

Figure 2:
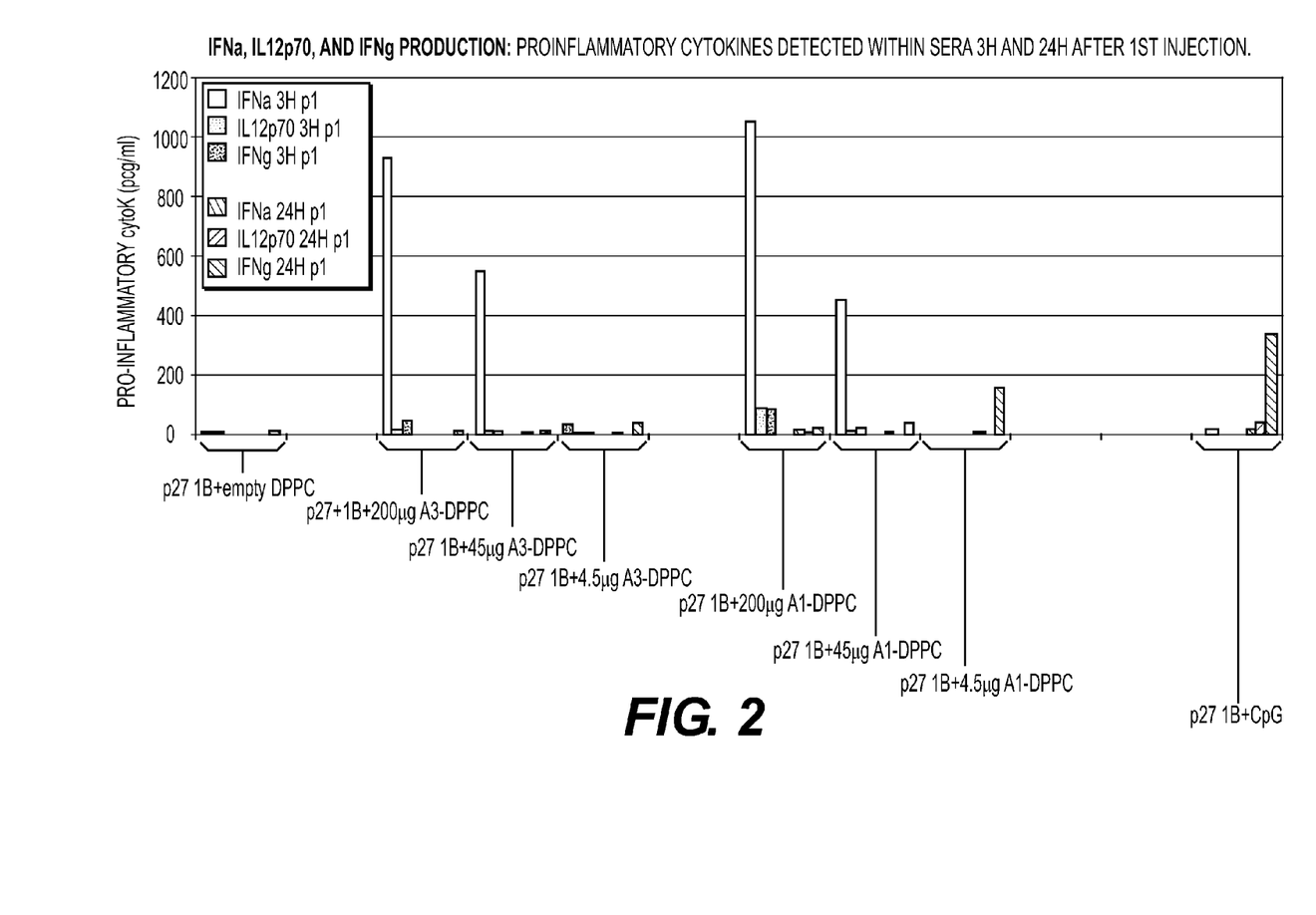
FIG. 2 shows Proinflamatory cytokines detected within sera following injection.
Figure 3:
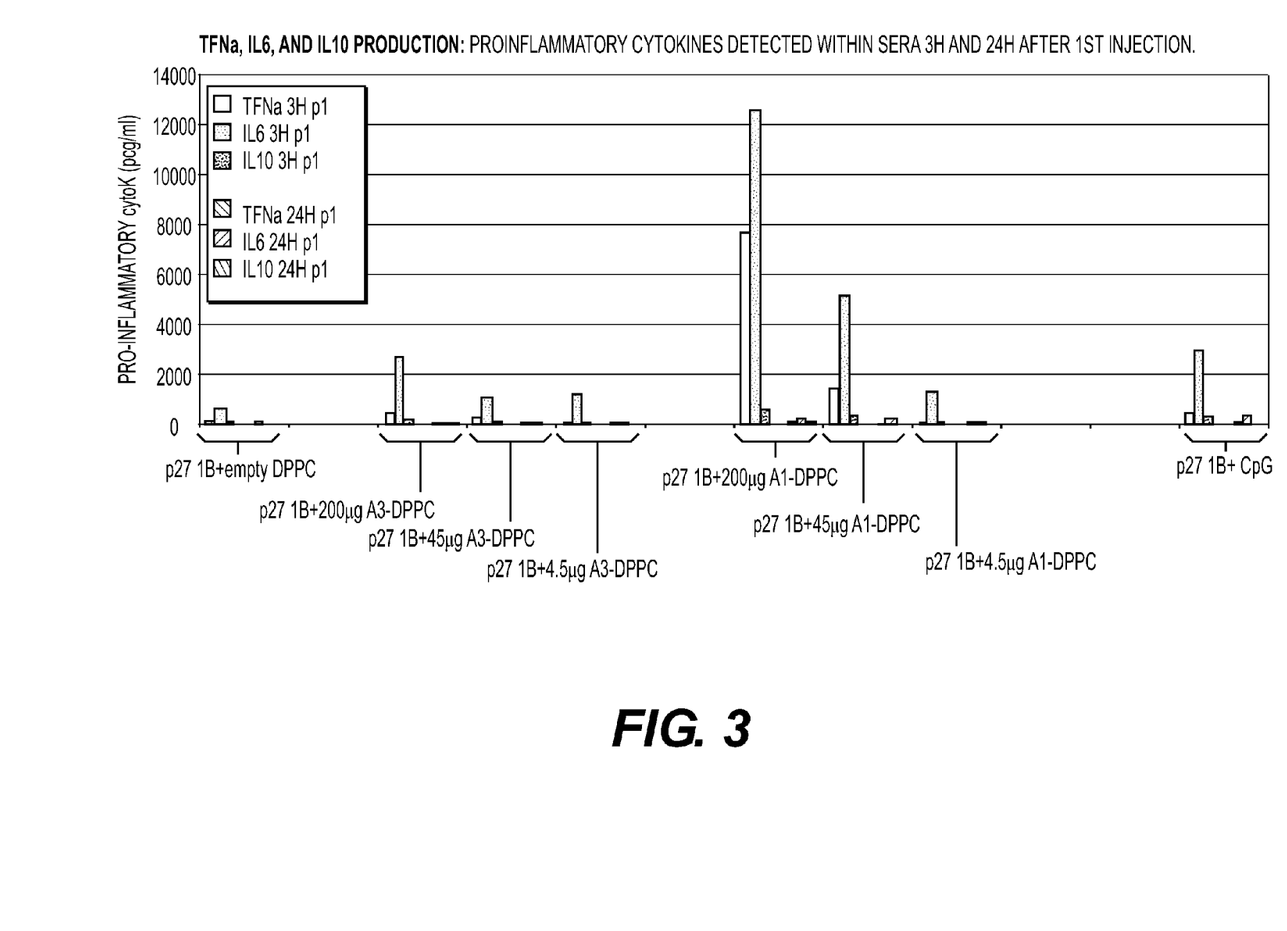
FIG. 3 shows Proinflamatory cytokines detected within sera following injection.
Figure 4:
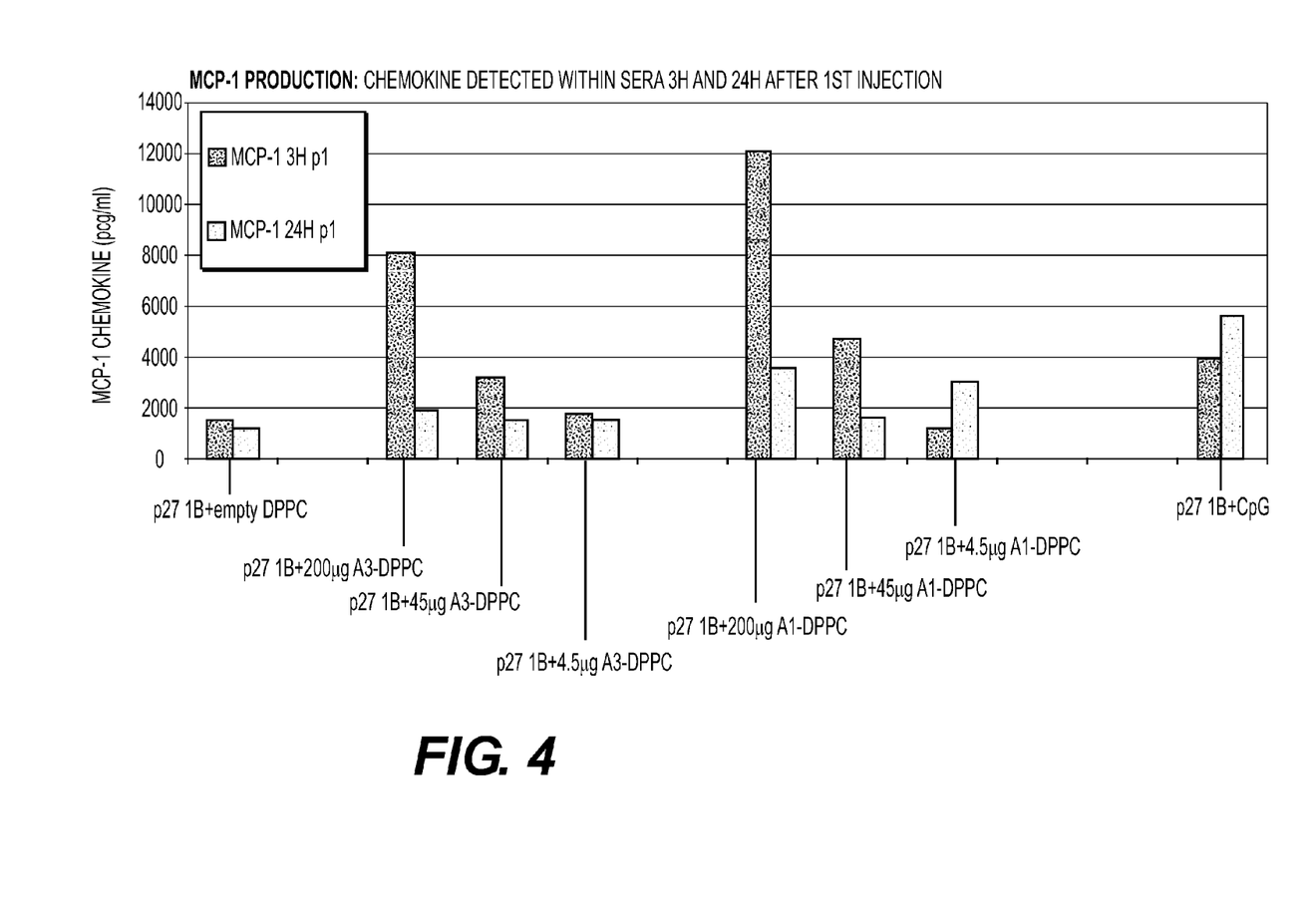
FIG. 4 shows Chemokines detected within sera following injection.

Other inflammatory cytokines such as TNF-α and IL-6 were enhanced when A3 or A1 were present in the formulations, A1 being more potent than A3 (FIG. 2). The chemokine MCP-1 was also enhanced in the presence of both compounds (FIG. 3). Altogether, these data show that the TLR7-L lipidated molecules are effective at inducing type I IFN and at enhancing the pro-inflammatory cytokine responses when combined to MPL/QS21 based formulation.

The TLR7-L molecules used here did not further enhanced the adaptative T-cell response as compared to the AS01 reference group (data not shown)

What is claimed is:

1. A compound according to the structure of Formula (I) comprising:

(I)

wherein
R$_1$ is selected from the group consisting of: C$_{1-6}$alkyl, C$_{1-6}$alkylamino, C$_{1-6}$alkoxy, C$_{3-6}$cycloalkylC$_{1-6}$alkyl, C$_{3-6}$cycloalkylC$_{1-6}$alkylamino, C$_{3-6}$cycloalkylC$_{1-6}$alkoxy, C$_{1-6}$alkoxyC$_{1-6}$alkyl, C$_{1-6}$alkoxyC$_{1-6}$alkylamino, C$_{1-6}$alkoxyC$_{1-6}$alkoxy; and optionally terminally substituted with a hydroxyl, amino, thio, hydrazino, hydrazido, azido, acetylenyl, carboxyl, or maleimido group;
n is 0 or an integer from 1-6;
Het is a four-, five-, or six-membered saturated heterocycle wherein
X, Y is CH or N, and at least one of X and Y is a nitrogen atom;
Q is O, NH, or covalent bond;
Z is O, CH$_2$, CF$_2$ or covalent bond;
W is O, S;
m is 0 or an integer from 1-6;
p is an integer from 1-2;
q is 0 or the integer 1;
A is or wherein
R$_2$ is H or straight, branched or unsaturated C$_4$-C$_{24}$ alkyl or acyl;
R$_3$ is straight, branched or unsaturated C$_4$-C$_{24}$ alkyl or acyl;
or a pharmaceutically acceptable salt thereof.

2. The compound according to the structure of Formula II:

(II)

wherein
R$_1$ is selected from the group consisting of C$_{1-6}$alkyl, C$_{1-6}$alkylamino, C$_{1-6}$alkoxy, C$_{3-6}$cycloalkylC$_{1-6}$alkyl, C$_{3-6}$cycloalkylC$_{1-6}$alkylamino, C$_{3-6}$cycloalkylC$_{1-6}$alkoxy, C$_{1-6}$alkoxyC$_{1-6}$alkyl, C$_{1-6}$alkoxyC$_{1-6}$alkylamino, C$_{1-6}$alkoxyC$_{1-6}$alkoxy;
n is 0 or an integer from 1-6;
X is CH or N;
Q is O, NH, or covalent bond;
Z is O, CH$_2$, CF$_2$ or covalent bond;
W is O, S;
m is 0 or an integer from 1-6;
p is an integer from 1-2;
q is 0 or the integer 1;
R$_2$ is H or straight, branched, or unsaturated C$_4$-C$_{24}$ alkyl or acyl;
R$_3$ is straight, branched or unsaturated C$_4$-C$_{24}$ alkyl or acyl;
or pharmaceutically acceptable salts thereof.

3. A compound according to the structure of Formula IX,

(IX)

wherein
R$_1$ is selected from the group consisting of C$_{1-6}$alkyl, C$_{1-6}$alkylamino, C$_{1-6}$alkoxy, C$_{1-6}$alkoxyC$_{1-6}$alkylamino, C$_{1-6}$alkoxyC$_{1-6}$alkoxy;

n is 0 or an integer between 1-2;
X is CH or N;
Q is O, NH, or covalent bond
m is 0 or an integer from 1-2;
q is 0
$R_2$ is H or straight, branched, or unsaturated $C_4$-$C_{24}$ alkyl or acyl, and
$R_3$ is straight, branched or unsaturated $C_4$-$C_{24}$ alkyl or acyl;
or pharmaceutically acceptable salts thereof.

4. The compound of claim 3 wherein
$R_1$ is $C_{1-6}$alkoxy or $C_{1-6}$alkoxy$C_{1-6}$alkyl
Q is O, NH
m is 0 or an integer from 1-2;
q is 0;
$R_2$ is H or straight, branched, or unsaturated $C_4$-$C_{24}$ alkyl or acyl, and
$R_3$ is straight, branched or unsaturated $C_4$-$C_{24}$ alkyl or acyl;
or pharmaceutically acceptable salts thereof.

5. A compound selected from the group consisting of (A1)

(A2)

(A3)

and;

or pharmaceutically acceptable salts thereof.

6. A compound according to the structure or pharmaceutically acceptable salts thereof.

7. A compound according to the structure or pharmaceutically acceptable salts thereof.

8. A compound according to the structure:

or pharmaceutically acceptable salts thereof.

9. A method of inducing an innate immune response in a mammal comprising administering a compound of claim 1.

10. The method of claim 9 wherein the response comprises inducing type 1 IFN.

11. The method of claim 9 wherein the response comprises enhancing pro-inflamatory cytokines.

12. The compound of claim 1 for use in a method of inducing an innate immune response, inducing a type 1 IFN response or enhancing pro-inflamatory cytokines.

* * * * *

UNITED STATES PATENT AND TRADEMARK OFFICE
CERTIFICATE OF CORRECTION

| | | |
|---|---|---|
| PATENT NO. | : 9,044,481 B2 | Page 1 of 1 |
| APPLICATION NO. | : 13/389307 | |
| DATED | : June 2, 2015 | |
| INVENTOR(S) | : David Johnson | |

It is certified that error appears in the above-identified patent and that said Letters Patent is hereby corrected as shown below:

In the Specification

At Column 1, Line 9 immediately after the first paragraph, insert:
-- STATEMENT REGARDING FEDERALLY SPONSORED RESEARCH
This invention was made with government support under Contract # HHSN272200900036C awarded by the National Institutes of Health. The government has certain rights in the invention. --

Signed and Sealed this
Twenty-sixth Day of November, 2024

Katherine Kelly Vidal
*Director of the United States Patent and Trademark Office*